US010660826B2

(12) United States Patent
Simonnet et al.

(10) Patent No.: US 10,660,826 B2
(45) Date of Patent: **\*May 26, 2020**

(54) SOLID COSMETIC COMPOSITION IN COMPACT POWDER FORM

(71) Applicant: L'ORÉAL, Paris (FR)

(72) Inventors: Anne Simonnet, Compiegne (FR); Stephane Masson, Compiegne (FR)

(73) Assignee: L'ORÉAL, Paris (FR)

( * ) Notice: Subject to any disclaimer, the term of this patent is extended or adjusted under 35 U.S.C. 154(b) by 0 days.

This patent is subject to a terminal disclaimer.

(21) Appl. No.: 15/830,180

(22) Filed: Dec. 4, 2017

(65) Prior Publication Data

US 2018/0092812 A1 Apr. 5, 2018

Related U.S. Application Data

(62) Division of application No. 13/885,285, filed as application No. PCT/EP2011/068895 on Oct. 27, 2011, now Pat. No. 10,034,817.

(60) Provisional application No. 61/419,900, filed on Dec. 6, 2010.

(30) Foreign Application Priority Data

Nov. 15, 2010 (FR) ...................................... 10 59353

(51) Int. Cl.
*A61K 8/00* (2006.01)
*A61K 8/02* (2006.01)
*A61K 8/25* (2006.01)
*A61K 8/26* (2006.01)
*A61K 8/34* (2006.01)
*A61K 8/37* (2006.01)
*A61K 8/49* (2006.01)
*A61K 8/73* (2006.01)
*A61K 8/891* (2006.01)
*A61K 8/895* (2006.01)
*A61Q 1/02* (2006.01)
*A61Q 1/10* (2006.01)
*A61Q 1/12* (2006.01)
*A61K 8/89* (2006.01)

(52) U.S. Cl.
CPC ................ *A61K 8/022* (2013.01); *A61K 8/25* (2013.01); *A61K 8/26* (2013.01); *A61K 8/345* (2013.01); *A61K 8/37* (2013.01); *A61K 8/375* (2013.01); *A61K 8/4973* (2013.01); *A61K 8/73* (2013.01); *A61K 8/732* (2013.01); *A61K 8/89* (2013.01); *A61K 8/891* (2013.01); *A61K 8/895* (2013.01); *A61Q 1/02* (2013.01); *A61Q 1/10* (2013.01); *A61Q 1/12* (2013.01); *A61K 2800/31* (2013.01)

(58) Field of Classification Search
CPC . A61K 8/022; A61K 8/25; A61K 8/26; A61K 8/345; A61K 8/37; A61K 8/375; A61K 8/4973; A61K 8/73; A61K 8/732; A61K 8/89; A61K 8/891; A61K 8/895; A61Q 1/02; A61Q 1/10; A61Q 1/12
See application file for complete search history.

(56) References Cited

U.S. PATENT DOCUMENTS

| | | | |
|---|---|---|---|
| 2001/0007672 A1 | 7/2001 | Miura et al. | |
| 2002/0012680 A1* | 1/2002 | Patel | A61K 9/4808 424/400 |
| 2002/0141958 A1 | 10/2002 | Maio et al. | |
| 2005/0008598 A1* | 1/2005 | Lu | A61K 8/0229 424/70.12 |
| 2005/0008599 A1 | 1/2005 | Lu et al. | |
| 2005/0220728 A1* | 10/2005 | Kanji | A61K 8/891 424/59 |
| 2005/0238596 A1 | 10/2005 | Imai | |
| 2009/0041698 A1 | 2/2009 | Cabiling et al. | |
| 2010/0083446 A1 | 4/2010 | Brun et al. | |
| 2011/0293548 A1* | 12/2011 | Caprarotta | A45D 40/16 424/69 |

FOREIGN PATENT DOCUMENTS

| | | | |
|---|---|---|---|
| EP | 0 976 388 A2 | 2/2000 | |
| EP | 1 226 811 A1 | 7/2002 | |
| EP | 1226811 A1 * | 7/2002 | ........... A61K 8/8152 |
| EP | 1 559 394 A1 | 8/2005 | |
| EP | 1 593 366 A1 | 11/2005 | |
| EP | 2 189 150 A1 | 5/2010 | |
| FR | 2 870 114 A1 | 11/2005 | |
| FR | 2 919 799 A1 | 2/2009 | |
| WO | WO 98/30195 A1 | 7/1998 | |
| WO | WO-9830195 A1 * | 7/1998 | ............... A61K 8/25 |

OTHER PUBLICATIONS

Pasquali et al. Some considerations about the hydrophilic-lipophilic balance system. Int J Pharm. May 22, 2008;356(1-2):44-51 (online 2007). (Year: 2008)*

(Continued)

*Primary Examiner* — Robert A Wax
*Assistant Examiner* — Olga V. Tcherkasskaya
(74) *Attorney, Agent, or Firm* — Oblon, McClelland, Maier & Neustadt, L.L.P.

(57) ABSTRACT

The present invention relates to a solid makeup and/or care cosmetic composition in the form of a compact powder, comprising, in a physiologically acceptable medium, at least:
  one pulverulent phase,
  one organopolysiloxane elastomer,
  one emulsifying system,
  one hydrophilic gelling agent, and
  one organic non-volatile oil present in a content of greater than or equal to 1% by weight relative to the total weight of the composition.
The invention also relates to an intermediate composition for the preparation of such a cosmetic composition, to a process for manufacturing this cosmetic composition, and to a process for coating the skin with the said cosmetic composition.

15 Claims, No Drawings

(56) References Cited

OTHER PUBLICATIONS

International Search Report dated May 10, 2012 in PCT/EP2011/068895.
"White Tiger Powder Compact" DATABASE GNPD [Online] Mintel Group Ltd, No. 1007748, XP 55003725, Nov. 1, 2008, 2 Pages.

* cited by examiner

SOLID COSMETIC COMPOSITION IN COMPACT POWDER FORM

CROSS-REFERENCE TO RELATED APPLICATIONS

This application is a divisional application of U.S. application Ser. No. 13/885,285, filed Oct. 29, 2013, pending, which is a National Stage application of PCT/EP2011/068895, filed Oct. 27, 2011, which claims the benefit of priority to U.S. provisional application 61/419,900, filed Dec. 6, 2010, and to French patent application 1059353 filed Nov. 15, 2010, the entire contents of which are incorporated herein by reference.

BACKGROUND OF THE INVENTION

Field of the Invention

The present invention targets the field of care and/or makeup cosmetic compositions, and more specifically compositions in compact powder form. The invention also relates to an intermediate composition for the preparation of such a cosmetic composition, to a process for manufacturing this cosmetic composition, and to a process for coating the skin with the said cosmetic composition.

The galenical forms conventionally adopted for solid compositions are generally loose, pressed or compact powders. As non-limiting illustrations of the solid galenical forms more particularly considered in the field of makeup, mention may be made especially of loose or pressed powders such as foundation powders, face powders and eyeshadows.

The function of the abovementioned powders is mainly to give colour, mattness and even, for those more particularly intended for facial skin, to improve the wear property of a foundation or, if used alone, to give coverage (foundation powder).

These galenical forms are particularly appreciated by users with regard to their lightness, softness, tack-free aspect or non-greasy feel.

In general, these compositions combine a pulverulent phase that is generally predominant with a binder phase usually featured by a liquid fatty phase. The pulverulent phase is formed essentially of fillers combined with pigments, the amount of these pigments being modified to afford the desired makeup effect, generally a colour effect.

To obtain a composition in solid, compacted form, it is known from the prior art to use compacted makeup powders formed by a mixture of powders with a fatty binder, which are put in form, for example, by compression.

However, these powders in particular have the drawback of being fragile. Thus, when the percentage of pigments or nacres increases in the product, its manufacture and its compacting become complicated or even impossible to perform at an industrial level given the quality and productivity requirements. In addition, the known compacted powders are generally brittle and often have poor impact strength, in particular when the degree of nacres incorporated is high, for example greater than or equal to 30%, or even 40%. Compositions having such a content of nacres have the disadvantage of being fragile and thus of breaking easily in the event of impacts.

Furthermore, if the amount of fatty binder is increased, this composition will have a tendency to become waxy, i.e. to harden during use to the point that it cannot be taken up.

It is known practice from the prior art, for the manufacture of such compositions, to use volatile organic solvents (isoparaffins, isododecane or isopropanol) used in an industrial process known as a Wet Process, so as to inject one or more foundation powder(s) into a respective cup. These solvents, with a flash point of less than 50° C., allow fluidization of the powder and thus its placing in form in the cup, and then evaporate off. However, this process may entail risks due to the release into the atmosphere of organic solvents.

Thus, in order to reduce these risks for the environment and the handler, the inventors have formulated a composition that is compatible with the use of such a process, using, not a hydrocarbon-based compound as volatile solvent, but water.

However, a problem encountered due to the use of water in such a process is the creation of very strong electrostatic bonds in the said composition, leading to the formation of a very cohesive composition in compact powder form that cannot be taken up sufficiently easily.

SUMMARY OF THE INVENTION

One aim of the present invention is thus to obtain makeup compositions in compact powder form that show good cohesion and good homogenization, while at the same time offering satisfactory cosmetic qualities, thus allowing a uniform makeup result, without any overthickness or any material effect.

An aim of the present invention is also to obtain impact-resistant makeup compositions in compact powder form.

An aim of the present invention is also to obtain makeup compositions in compact powder form that show good adhesion to the keratin material to be made up, in particular the eyelids.

An aim of the present invention is also to offer twofold use (wet and dry) for a modulable long-lasting makeup. In particular, an aim of the invention is to allow the production of a powdery rendering during dry application of the makeup composition, and a creamy rendering during wet application of this same composition, thus making it possible to vary the optical effects on application.

An aim of the invention is also to obtain makeup compositions in compact powder form obtained by means of an industrial process that is safe for the manufacturer and environmentally friendly.

To do this, according to a first aspect, one subject of the present invention is a solid makeup and/or care cosmetic composition in the form of a compact powder, comprising, in a physiologically acceptable medium, at least:
- one pulverulent phase,
- one organopolysiloxane elastomer,
- one emulsifying system,
- one hydrophilic gelling agent, the said composition comprising an organic non-volatile oil present in a content of greater than or equal to 1% by weight relative to the total weight of the composition, preferably 2% by weight relative to the total weight of the composition.

DETAILED DESCRIPTION OF THE INVENTION

Preferably, the said non-volatile oil is chosen from hydrocarbon-based and silicone non-volatile oils, and a mixture thereof. Such a composition preferably obtained via an injection manufacturing process using water as dilution solvent in particular has the advantage of allowing good structuring of the powder.

Such a composition can thus produce eyeshadows comprising a large content of colouring agents such as pigments and/or nacres, for example greater than 50% by weight relative to the total weight of the composition, without weakening the product, and while conserving good uptake qualities.

Furthermore, such a powder formed by virtue of the presence of water, even if there is little or no trace of this water in the final product after the drying step, makes it possible to conserve a composition that is suitable for rehydration. This principle makes the product ideal for wet or dry use.

The texture of such a composition permits the deposition of a smooth and homogeneous film on the skin, which has good wear properties. Finally, this compact composition, despite the possible significant presence of colouring agents, remains particularly resistant to impacts.

The composition according to the invention preferably comprises as pulverulent phase at least one filler, the said filler and the said hydrophilic gelling agent preferably being distinct.

For the purposes of the present invention, the following definitions apply:

"solid" means the state of the composition at room temperature (25° C.) and at atmospheric pressure (760 mmHg), i.e. a composition of high consistency, which conserves its form during storage. As opposed to "fluid" compositions, it does not flow under its own weight. It is advantageously characterized by a hardness as defined below.

"compact powder" means a mass of product whose cohesion is at least partly provided by compacting or pressing during the manufacture. In particular, by taking a measurement using a TA.XT.plus Texture Analyser texturometer sold by the company Stable Micro Systems, the compact powder according to the invention may advantageously have a pressure resistance of between 0.2 kg and 2.5 kg and especially between 0.8 kg and 1.5 kg, relative to the surface area of the spindle used (in the present case 7.07 mm$^2$). The measurement of this resistance is performed by moving an SMS P/3 flat-headed cylindrical spindle over a distance of 1.5 mm and at a speed of 0.5 mm/sec.

"physiologically acceptable medium" is intended to denote a medium that is particularly suitable for the application of a composition according to the invention to the skin.

The composition according to the invention preferably comprises less than 3% by weight of water relative to the total weight of the composition, preferably less than 2% by weight of water, or is even free of water.

The composition according to the invention advantageously comprises a solids content of greater than or equal to 90%, better still 95%, or even, more preferentially still, 97%.

For the purposes of the present invention, the "solids content" denotes the content of non-volatile matter.

The solids content (abbreviated as SC) of a composition according to the invention is measured using a "Halogen Moisture Analyzer HR 73" commercial halogen desiccator from Mettler Toledo. The measurement is performed on the basis of the weight loss of a sample dried by halogen heating, and thus represents the percentage of residual matter once the water and the volatile matter have evaporated off.

This technique is fully described in the machine documentation supplied by Mettler Toledo.

The measuring protocol is as follows:

Approximately 2 g of the composition, referred to hereinbelow as the sample, are spread out on a metal crucible, which is placed in the halogen desiccator mentioned above. The sample is then subjected to a temperature of 105° C. until a constant weight is obtained. The wet mass of the sample, corresponding to its initial mass, and the dry mass of the sample, corresponding to its mass after halogen heating, are measured using a precision balance.

The experimental error associated with the measurement is of the order of plus or minus 2%.

The solids content is calculated in the following manner:

Solids content (expressed as weight percentage)= 100×(dry mass/wet mass).

The composition may comprise a pulverulent phase in an amount of greater than or equal to 35% by weight relative to the total weight of the composition. The pulverulent phase may comprise a filler and a colouring agent chosen from nacres, pigments and reflective particles, and mixtures thereof. The said composition may have a content of nacres of between 30% and 70% by weight relative to the total weight of the composition, advantageously greater than or equal to 40% by weight relative to the total weight of the composition, better still 50%, or even 55%.

According to one particular embodiment, the emulsifying system of the composition is chosen from at least one nonionic surfactant with an HLB of less than 8 at 25° C., an anionic surfactant, a cationic surfactant and an amphoteric surfactant, and mixtures thereof. Advantageously, the said surfactant is chosen from saccharide esters and ethers, fatty acid esters, oxyalkylenated alcohols, fatty alcohols and silicone compounds. Preferably, the said surfactant is chosen from saccharide esters and ethers.

According to one particular embodiment, the said surfactant is chosen from an emulsifying organopolysiloxane elastomer, advantageously from polyglycerolated organopolysiloxane elastomers and polyoxyalkylenated organopolysiloxane elastomers.

As a variant or additionally, the said composition may comprise a non-emulsifying organopolysiloxane elastomer.

The said organopolysiloxane elastomer may be present in a solids content of between 0.5% and 8% relative to the total weight of the composition.

The said hydrophilic gelling agent may be chosen from thickening fillers, polymeric thickeners and associative polymers.

According to one particular embodiment, the said composition comprises a chelating agent, advantageously chosen from aminocarboxylic acids such as tetrasodium EDTA.

Preferably, the composition according to the invention is an eyeshadow, an eyebrow composition, a blusher or a face powder. Even more preferentially, the composition is an eyeshadow.

According to one particularly preferred embodiment, the said solid makeup and/or care cosmetic composition that is in the form of a compact powder comprises, in a physiologically acceptable medium, limits inclusive and expressed as weight of solids for each of the compounds considered, relative to the total weight of the composition, at least:

0.5% to 3% of an emulsifying system, in particular at least one nonionic surfactant with an HLB of less than 8, such as sorbitan stearate, 1% to 3% of a hydrophilic gelling agent, in particular at least one thickening filler such as a clay, 1% to 20% of a non-volatile oil, advantageously chosen from hydrocarbon-based and silicone oils, and a mixture thereof, for example a non-volatile silicone oil of INCI name dimethicone, 0.5% to 10% of an organopolysiloxane elastomer, in particular at least one elastomer conveyed in at least one non-volatile silicone oil, for example an elastomer of INCI name dimethicone/vinyl dimethicone copolymer, 50% to 70% of colouring agents, in particular chosen from at least one nacre, and 0 to 3% of water.

According to a second aspect of the invention, a composition according to the invention is preferably obtained from an intermediate composition. Such an intermediate composition intended to be injection-moulded preferably comprises a non-volatile phase, corresponding to the components found in the composition to be applied by the user, and a volatile phase, preferably formed from water, used as solvent to allow the injection moulding of the said composition, which is intended to be at least partially or even totally removed from the said composition to be applied by the user. This intermediate composition has a water content of 30% to 50% by weight relative to the total weight of the composition. It also preferably comprises a non-volatile phase, present in a content of 50% to 70% by weight relative to the total weight of the composition.

Such a composition is intended to be passed through a machine such as the Pilote Back Injection Machine sold by the company Nanyo Co. Ltd (Japan). This composition is injected into one or more moulds, or cups, from which the water conveying the pulverulent phase is then removed. This water may advantageously be removed by placing under vacuum and/or stoving and/or drying by microwave irradiation and/or lyophilization and/or drying by infrared irradiation. The advantage of such machines is that they can be fitted with several injection heads, thus making it possible to easily and simultaneously prepare several different compositions in compact powder form, for example of different shades.

According to a third aspect, a subject of the present invention is also a process for manufacturing a makeup and/or care cosmetic composition from an intermediate composition as defined above. This process comprises the steps:

of injection into a cup or mould, preferably via its base, of the said intermediate composition, and of removal of the aqueous phase from the said intermediate composition, preferably at least partly simultaneously with the said injection step, via any suitable means.

The step of removing the aqueous phase may preferably be performed via a step of placing the said composition under vacuum, which preferably takes place simultaneously with the injection step, preferably followed, once the injection step is complete, by a step of oven-drying until the weight of the said makeup and/or care composition is stable.

According to a fourth aspect, a subject of the present invention is also a process for making up or caring for keratin materials, in particular the skin and especially eyelids, in which a composition as defined previously is applied to the said keratin materials.

Pulverulent Phase

The pulverulent phase comprises fillers and colouring agents.

A solid composition according to the invention advantageously has a content of pulverulent phase of greater than or equal to 35% by weight, in particular greater than or equal to 40% by weight, more particularly ranging from 45% to 90% by weight and better still from 50% to 70% by weight relative to its total weight.

Fillers

The term "fillers" should be understood as meaning colourless or white solid particles of any form, which are in a form that is insoluble and dispersed in the medium of the composition. These fillers, of mineral or organic nature, give the composition softness and give the makeup result a matt effect and uniformity.

The fillers used in the compositions according to the present invention may be of lamellar, globular or spherical form, fibres or in any form intermediate between these defined forms.

The fillers according to the invention may or may not be surface-coated, and in particular they may be surface-treated with silicones, amino acids, fluoro derivatives or any other substance that promotes the dispersion and compatibility of the filler in the composition.

Among the mineral fillers that may be used in the compositions according to the invention, mention may be made of talc, mica, silica, magnesium aluminium silicate, trimethyl siloxysilicate, kaolin, bentone, calcium carbonate, magnesium hydrogen carbonate, hydroxyapatite, boron nitride, hollow silica microspheres (Silica Beads from Maprecos), glass or ceramic microcapsules, silica-based fillers, for instance Aerosil 200 or Aerosil 300; Sunsphere L-33 and Sunsphere H-51 sold by Asahi Glass; Chemicelen sold by Asahi Chemical; composites of silica and of titanium dioxide, for instance the TSG series sold by Nippon Sheet Glass, perlite powders and fluorphlogopite, and mixtures thereof.

Among the organic fillers that may be used, mention may be made of polyamide powders (sold under trademark Nylon® Orgasol from Atochem), poly-β-alanine powders and polyethylene powders, polytetrafluoroethylene powders (sold under trademark Teflon®), lauroyllysine, starch, tetrafluoroethylene polymer powders, hollow polymer microspheres, for example comprising an (alkyl)acrylate, sold under trademark such as Expancel® (Nobel Industrie), metal soaps derived from organic carboxylic acids containing from 8 to 22 carbon atoms and preferably from 12 to 18 carbon atoms, for example zinc stearate, magnesium stearate, lithium stearate, zinc laurate, magnesium myristate, sold under trademark Polypore® L200 (Chemdal Corporation), silicone resin microbeads (for example sold under trademark Tospearl® from Toshiba), polyurethane powders, in particular powders of crosslinked polyurethane comprising a copolymer, the said copolymer comprising trimethylol hexyl lactone, for instance the hexamethylene diisocyanate/trimethylol hexyl lactone polymer sold under the trademark Plastic Powder D-400® or Plastic Powder D-800® by the company Toshiki, carnauba microwaxes, such as the product sold under the trademark Micro Care 350® by the company Micro Powders, synthetic microwaxes, such as the product sold under the trademark MicroEase 114S® by the company Micro Powders, microwaxes formed from a mixture of carnauba wax and polyethylene wax, such as those sold sold under trademark Micro Care 300® and 310® by the company Micro Powders, microwaxes formed from a mixture of carnauba wax and of synthetic wax, such as the product sold under the trademark Micro Care 325® by the company Micro Powders, polyethylene microwaxes, such as those sold under the trademarks Micropoly 200®, 220®, 220L® and 250S® by the company Micro Powders; fibres of synthetic or natural, mineral or organic origin. They may be short or long, individual or organized, for example braided, and hollow or solid. They may have any shape and may especially have a circular or polygonal (square, hexagonal or octagonal) cross section depending on the specific application envisaged. In particular, their ends are blunted and/or polished to prevent injury. The fibres have a length ranging from 1 µm to 10 mm, preferably from 0.1 mm to 5 mm and better still from 0.3 mm to 3 mm. Their cross section may be included in a circle with a diameter ranging from 2 nm to 500 µm, preferably ranging from 100 nm to 100 µm and better still from 1 µm to 50 µm. As fibres that may be used in the compositions according to the invention, mention may be made of non-rigid fibres such as polyamide (Nylon®) fibres or rigid fibres such as polyimideamide fibres, for instance those sold under the trademarks Kemiel® and Kermel Tech® by the company Rhodia or poly(p-phenyleneterephthalamide) (or aramid) fibres sold especially under the trademarks name Kevlar® by the company DuPont de Nemours, and mixtures thereof.

As representatives of such fillers preferably used in the context of the present invention, mention may be made especially of talc, starch, fluorphlogopite, clays such as magnesium aluminium silicate, or hollow polymer microspheres.

The fillers may be present in the composition in a content ranging from 5% to 60% by weight and preferably from 10% to 25% by weight relative to the total weight of the composition.

As stated above, a composition according to the invention preferably also comprises a colouring agent in its pulverulent phase.

Colouring Agents

The coloring agent or dyestuff according to the invention is preferably chosen from pigments, nacres and reflective particles, and mixtures thereof.

Pigments

The term "pigments" should be understood as meaning white or coloured, mineral or organic particles of any shape, which are insoluble in the physiological medium, and which are intended to colour the composition.

The pigments may be white or coloured, and mineral and/or organic.

Among the mineral pigments that may be mentioned are titanium dioxide, optionally surface-treated, zirconium oxide or cerium oxide, and also zinc oxide, iron (black, yellow or red) oxide or chromium oxide, manganese violet, ultramarine blue, chromium hydrate and ferric blue, and metal powders, for instance aluminum powder and copper powder.

The organic pigments may be chosen from the materials below, and mixtures thereof:

cochineal carmine, organic pigments of azo dyes, anthraquinone dyes, indigoid dyes, xanthene dyes, pyrene dyes, quinoline dyes, triphenylmethane dyes and fluorane dyes. Among the organic pigments, mention may be made especially of the D&C certified pigments known under the following names: D&C Blue No. 4, D&C Brown No. 1, D&C Green No. 5, D&C Green No. 6, D&C Orange No. 4, D&C Orange No. 5, D&C Orange No. 10, D&C Orange No. 11, D&C Red No. 6, D&C Red No. 7, D&C Red No. 17, D&C Red No. 21, D&C Red No. 22, D&C Red No. 27, D&C Red No. 28, D&C Red No. 30, D&C Red No. 31, D&C Red No. 33, D&C Red No. 34, D&C Red No. 36, D&C Violet No. 2, D&C Yellow No. 7, D&C Yellow No. 8, D&C Yellow No. 10, D&C Yellow No. 11, FD&C Blue No. 1, FD&C Green No. 3, FD&C Red No. 40, FD&C Yellow No. 5, FD&C Yellow No. 6.

The chemical materials corresponding to each of the organic dyestuffs mentioned previously are mentioned in the *International Cosmetic Ingredient Dictionary and Handbook*, 1997 edition, pages 371 to 386 and 524 to 528, published by The Cosmetic, Toiletries and Fragrance Association.

A composition according to the invention may comprise a content of pigments ranging from 0 to 60% by weight relative to the total weight of the composition, preferably ranging from 5% to 30% by weight and preferentially ranging from 10% to 20% by weight, relative to the total weight of the composition.

Nacres

The terms "nacres" should be understood as meaning coloured particles of any form, which may or may not be iridescent, especially produced by certain molluscs in their shell, or alternatively synthesized, and which have a colour effect via optical interference.

Examples of nacres that may be mentioned include nacreous pigments such as titanium mica coated with an iron oxide, mica coated with bismuth oxychloride, titanium mica coated with chromium oxide, and also nacreous pigments based on bismuth oxychloride. They may also be mica particles at the surface of which are superposed at least two successive layers of metal oxides and/or of organic dyestuffs.

The nacres may more particularly have a yellow, pink, red, bronze, orange, brown, gold and/or coppery colour or tint.

As illustrations of nacres that may be introduced as interference pigments into the first composition, mention may be made especially of the gold-coloured nacres sold especially by the company Engelhard under the name Brilliant gold 212G (Timica), Gold 222C (Cloisonne), Sparkle gold (Timica), Gold 4504 (Chromalite) and Monarch gold 233X (Cloisonne); the bronze nacres sold especially by the company Merck under the name Bronze fine (17384) (Colorona) and Bronze (17353) (Colorona) and by the company Engelhard under the name Super bronze (Cloisonne); the orange nacres sold especially by the company Engelhard under the name Orange 363C (Cloisonne) and Orange MCR 101 (Cosmica) and by the company Merck under the name Passion orange (Colorona) and Matte orange (17449) (Microna); the brown nacres sold especially by the company Engelhard under the name Nu-antique copper 340XB (Cloisonne) and Brown CL4509 (Chromalite); the nacres with a copper tint sold especially by the company Engelhard under the name Copper 340A (Timica); the nacres with a red tint sold especially by the company Merck under the name Sienna fine (17386) (Colorona); the nacres with a yellow tint sold especially by the company Engelhard under the name Yellow (4502) (Chromalite); the red nacres with a gold tint sold especially by the company Engelhard under the name Sunstone G012 (Gemtone); the pink nacres sold especially by the company Engelhard under the name Tan opale G005 (Gemtone); the black nacres with a gold tint sold especially by the company Engelhard under the name Nu antique bronze 240 AB (Timica), the blue nacres sold especially by the company Merck under the name Matte blue (17433) (Microna), the white nacres with a silvery tint sold especially by the company Merck under the name Xirona Silver, and the golden-green pink-orange nacres sold especially by the company Merck under the name Indian summer (Xirona), and mixtures thereof.

Still as examples of nacres, mention may also be made of particles comprising a borosilicate substrate coated with titanium oxide.

Particles having a glass substrate coated with titanium oxide are especially sold under the name Metashine MC1080RY by the company Toyal.

Finally, examples of nacres that may also be mentioned include polyethylene terephthalate flakes, especially those sold by the company Meadowbrook Inventions under the name Silver 1P 0.004X0.004 (silver flakes).

The compositions according to the invention may comprise, limits inclusive, from 10% to 80%, for example from 20% to 70% and better still from 30% to 60% by weight of nacres relative to the total weight of colouring agents. In particular, they may comprise a content of greater than or equal to 50% by weight of nacres relative to the total weight of colouring agents.

The compositions according to the invention may comprise from 20% to 90%, for example from 30% to 80% and better still from 50% to 75% by weight of nacres relative to the total weight of the pulverulent phase. In particular, they may comprise a content of greater than or equal to 50% by weight of nacres relative to the total weight of the pulverulent phase.

The compositions according to the invention may comprise from 10 to 80%, for example from 20% to 70% and better still from 30% to 60% by weight of nacres relative to the total weight of the composition. In particular, they may comprise a content of greater than or equal to 50% by weight relative to the total weight of the composition.

Reflective Particles

The term "reflective particles" denotes particles whose size, structure, especially the thickness of the layer(s) of which they are made and their physical and chemical nature, and surface state, allow them to reflect incident light. This reflection may, where appropriate, have an intensity sufficient to create at the surface of the composition or of the mixture, when it is applied to the support to be made up, points of overbrightness that are visible to the naked eye, i.e. more luminous points that contrast with their environment by appearing to sparkle.

The reflective particles may be selected so as not to significantly alter the colouration effect generated by the colouring agents with which they are combined, and more particularly so as to optimize this effect in terms of colour yield. They may more particularly have a yellow, pink, red, bronze, orange, brown, gold and/or coppery colour or tint.

These particles may have varied forms and may especially be in platelet or globular form, in particular spherical.

Irrespective of their form, the reflective particles may or may not have a multilayer structure, and, in the case of a multilayer structure, for example at least one layer of uniform thickness, especially a reflective material.

When the reflective particles do not have a multilayer structure, they may be composed, for example, of metal oxides, especially titanium or iron oxides obtained synthetically.

When the reflective particles have a multilayer structure, they may comprise, for example, a natural or synthetic substrate, especially a synthetic substrate at least partially coated with at least one layer of a reflective material, especially of at least one metal or metallic material. The substrate may be a monomaterial, multimaterial, organic and/or mineral substrate.

More particularly, it may be chosen from glasses, ceramics, graphite, metal oxides, aluminas, silicas, silicates, especially aluminosilicates and borosilicates, and synthetic mica, and mixtures thereof, this list not being limiting.

The reflective material may comprise a layer of metal or of a metallic material.

Reflective particles are described especially in documents JP-A-09188830, JP-A-10158450, JP-A-10158541, JP-A-07258460 and JP-A-05017710.

Again as an example of reflective particles comprising a mineral substrate coated with a layer of metal, mention may also be made of particles comprising a silver-coated borosilicate substrate.

Particles with a silver-coated glass substrate, in the form of platelets, are sold under the name Microglass Metashine REFSX 2025 PS by the company Toyal. Particles with a glass substrate coated with nickel/chromium/molybdenum alloy are sold under the name Crystal Star GF 550 and GF 2525 by this same company.

Particles comprising a metallic substrate such as silver, aluminum, iron, chromium, nickel, molybdenum, gold, copper, zinc, tin, manganese, steel, bronze or titanium, may also be used, said substrate being coated with at least one layer of at least one metal oxide such as titanium oxide, aluminum oxide, iron oxide, cerium oxide, chromium oxide or silicon oxides, and mixtures thereof.

Examples that may be mentioned include aluminium powder, bronze powder or copper powder coated with SiO2 sold under the name Visionaire by the company Eckart.

Preferably, the pulverulent phase comprises at least one compound chosen from:
organic pigments such as, for example:
    the pigments certified D&C by the Food & Drug Administration as listed in the section "Color Additives—Batch Certified by the U.S. Food and Drug Administration" of the CTFA; mention may be made especially of Blue 1 and 4, Brown 1, Ext. Violet 2, Ext. Yellow 7, Green 3, 5, 6 and 8, Orange 4, 5, 10 and 11, Red 4, 6, 7, 17, 21, 22, 27, 28, 30, 36 and 40, Violet 2, Yellow 5, 6, 7, 8, 10 and 11,
mineral pigments such as:
    iron oxide, titanium oxide, zirconium oxide, cerium oxide, zinc oxide, iron oxide or chromium oxide,
    ferric blue, manganese violet, ultramarine blue, pink or violet, chromium hydrate, chromium hydroxide or bismuth oxychloride,
nacres such as, for example:
    mica coated with titanium oxide, mica coated with titanium oxide and iron oxide, and mica coated with an amino acid such as lauroyl lysine,
    polyethylene terephthalate flakes,
    sericite,
    and mixtures thereof,
reflective particles such as, for example:
    particles comprising a borosilicate substrate coated with a metallic layer.

Aqueous Phase

The intermediate composition used in the injection-moulding process according to the invention comprises an aqueous phase in a proportion of from 30% to 50% by weight relative to the total weight of the composition.

This aqueous phase is subsequently at least partly removed in the said composition to be applied by the user, which may finally comprise less than 3% by weight of water relative to the total weight of the composition, or even less than 2% by weight of water, or alternatively is free of water. This removal of water may be performed by any suitable means. It may especially be performed, as a variant or additionally, placing under vacuum, oven-drying, ventilation, lyophilization or heating, or alternatively by microwave or infrared radiation. According to one preferred embodiment, this water removal step takes place by suction via a system for placing under vacuum the said intermediate composition present in the cup, and also during a step of drying in a ventilated oven, for example at 50° C., of the said intermediate composition until the weight of the said composition no longer changes.

The composition according to the invention thus generally comprises an aqueous phase, which may be termed residual, corresponding to the content of water not removed during the injection-moulding step.

This aqueous phase, when present, is used in an amount that is compatible with the pulverulent galenical form required according to the invention.

The aqueous phase may be a demineralized water or alternatively a floral water such as cornflower water and/or a mineral water such as Vittel water, Lucas water or La Roche Posay water and/or a spring water.

The aqueous phase may also comprise a polyol that is miscible with water at room temperature (25° C.) chosen especially from polyols especially containing from 2 to carbon atoms, preferably containing from 2 to 10 carbon atoms and preferentially containing from 2 to 6 carbon atoms, such as glycerol, propylene glycol, butylene glycol, pentylene glycol, hexylene glycol, dipropylene glycol or diethylene glycol; glycol ethers (especially containing from 3 to 16 carbon atoms) such as mono-, di- or tripropylene glycol ($C_1$-$C_4$) alkyl ethers or mono-, di- or triethylene glycol ($C_1$-$C_4$) alkyl ethers; and mixtures thereof.

The composition according to the invention may comprise a polyol that is miscible with water at room temperature. Such polyols may promote the moisturization of the cutaneous surface onto which the composition is applied.

In addition, the composition according to the invention may comprise a monoalcohol containing from 2 to 6 carbon atoms, such as ethanol or isopropanol.

Hydrophilic Gelling Agents

The composition according to the invention comprises one or more hydrophilic gelling agent(s).

For the purposes of the present patent application, the term "hydrophilic gelling agent" means a compound that is capable of gelling the aqueous phase of the compositions according to the invention. More particularly, the function of these hydrophilic gelling agents is to structure the aqueous phase of the intermediate composition, so as to maintain a structured composition once the water has been removed from the said composition. This gelling agent may be introduced with the aqueous phase of the intermediate composition or with the pulverulent phase. This gelling agent is advantageously soluble in the aqueous phase of the intermediate composition.

The gelling agent that may be used according to the invention may especially be characterized by its capacity to form in water, beyond a certain concentration C*, a gel characterized by oscillatory rheology ($\mu$=1 Hz) by a flow threshold $\tau_c$ at least equal to 10 Pa. This concentration C* may vary widely according to the nature of the gelling polymer under consideration.

The gelling agent may be present in the composition in an amount that is sufficient to adjust the stiffness modulus G* (1 Hz, 25° C.) of the composition to a value greater than or equal to 10 000 Pa and especially ranging from 10 000 Pa to 100 000 Pa.

The method for measuring these parameters of the composition is described, for example, in patent application EP 1 534 218 in the paragraph entitled "rheological characterization".

It is understood that the alkali metal, alkaline-earth metal or transition metal salts, such as zinc stearate, zinc myristate or magnesium stearate are not considered within the meaning of the present invention as hydrophilic gelling agents. Specifically, such compounds serve first and foremost as fillers, and in particular as agents for compacting the pulverulent phase.

Thickening Fillers

Thickening fillers may fulfil this function as aqueous-phase gelling agents. Such fillers preferably comprise a clay that is capable of swelling in water and/or hollow mineral or organic microspheres.

The clay present in the composition according to the invention is clay that is capable of swelling in water; this clay swells in water and forms after hydration a colloidal dispersion.

Clays are products that are already well known per se, which are described, for example, in the publication Minéralogie des argiles [Mineralogy of Clays], S. Caillère, S. Hénin, M. Rautureau, 2nd Edition 1982, Masson.

Clays are silicates containing a cation advantageously chosen from calcium, magnesium, aluminium, sodium, potassium and lithium cations, and mixtures thereof.

Examples of such products that may be mentioned include clays of the smectite family such as montmorillonites, hectorites, bentonites, beidellites and saponites, and also of the vermiculite, stevensite and chlorite families.

These clays may be of natural or synthetic origin. Clays that are cosmetically compatible and acceptable with the skin are preferably used.

According to one particularly preferred embodiment of the present invention, the clay used, that is capable of swelling in water, is chosen from montmorillonites, hectorites, bentonites, beidellite and saponites, and more particularly hectorites and bentonites.

As clays that are capable of swelling in water which may be used according to the invention, mention may be made of synthetic hectorites (also known as laponites), for instance the products sold by the company Laporte under the name Laponite XLG, Laponite RD and Laponite RDS (these products are sodium magnesium silicates and in particular sodium lithium magnesium silicates); bentonites, for instance the product sold under the name Bentone HC by the company Rheox; magnesium aluminium silicates, especially hydrated, for instance the product sold by the Vanderbilt Company under the name Veegum Ultra, or calcium silicates and especially the product in synthetic form sold by the company under the name Micro-cel C.

Preferably, when a thickening filler is used as hydrophilic gelling agent, such as a clay, at least one distinct additional filler is provided in the said pulverulent phase of the composition.

The clay may be present in the composition in a content ranging from 0.5% to 5% by weight and better still from 1% to 3% by weight relative to the total weight of the composition.

Polymeric Hydrophilic Thickeners

More particularly, this gelling agent may be chosen from the following polymeric thickeners:

acrylic or methacrylic acid homopolymers or copolymers or salts and esters thereof and in particular the products sold under the names Versicol F or Versicol K by the company Allied Colloid, Ultrahold 8 by the company Ciba-Geigy, and polyacrylic acids of Synthalen K type, and salts, especially sodium salts, of polyacrylic acids (corresponding to the INCI name sodium acrylate copolymer) and more particularly a crosslinked sodium polyacrylate (corresponding to the INCI name sodium acrylate copolymer (and) caprylic/capric triglycerides) sold under the name Luvigel EM by the company, copolymers of acrylic acid and of acrylamide sold in the form of the sodium salt thereof under the names Reten by the company Hercules, the sodium polymethacrylate sold under the name Darvan No. 7 by the company Vanderbilt, and the sodium salts of polyhydroxycarboxylic acids sold under the name Hydagen F by the company Henkel, polyacrylic acid/alkyl acrylate copolymers, preferably modified or unmodified carboxyvinyl polymers; the copolymers most particularly preferred according to the present invention are acrylate/$C_{10}$-$C_{30}$-alkylacrylate copolymers (INCI name: Acrylates/$C_{10-30}$ Alkyl acrylate Crosspolymer) such as the products sold by the company Lubrizol under the trade names Pemulen TR1, Pemulen TR2, Carbopol 1382 and Carbopol ETD 2020, and even more preferentially Pemulen TR-2;

AMPS (polyacrylamidomethylpropanesulfonic acid partially neutralized with aqueous ammonia and highly crosslinked) sold by the company Clariant, AMPS/acrylamide copolymers such as the products Sepigel or Simulgel sold by the company SEPPIC, especially a copolymer of INCI name Polyacrylamide (and) C13-14 Isoparaffin (and) Laureth-7.

polyoxyethylenated AMPS/alkyl methacrylate copolymers (crosslinked or non-crosslinked) of the type such as Aristoflex HMS sold by the company Clariant, and mixtures thereof.

Other examples of polymeric thickeners that may be mentioned include:

anionic, cationic, amphoteric or nonionic chitin or chitosan polymers;

cellulose polymers, other than alkylcellulose, chosen from hydroxyethylcellulose, hydroxypropylcellulose, hydroxymethylcellulose, ethylhydroxyethylcellulose and carboxymethylcellulose, and also quaternized cellulose derivatives;

vinyl polymers, for instance polyvinylpyrrolidones, copolymers of methyl vinyl ether and of malic anhydride, the copolymer of vinyl acetate and of crotonic acid, copolymers of vinylpyrrolidone and of vinyl acetate; copolymers of vinylpyrrolidone and of caprolactam; polyvinyl alcohol;

optionally modified polymers of natural origin, such as: galactomannans and derivatives thereof, such as konjac gum, gellan gum, locust bean gum, fenugreek gum, karaya gum, gum tragacanth, gum arabic, acacia gum, guar gum, hydroxypropyl guar, hydroxypropyl guar modified with sodium methylcarboxylate groups (Jaguar XC97-1, Rhodia), hydroxypropyltrimethylammonium guar chloride, and xanthan derivatives;

alginates and carrageenans;

glycoaminoglycans, hyaluronic acid and derivatives thereof;

deoxyribonucleic acid;

mucopolysaccharides such as hyaluronic acid and chondroitin sulfates, and mixtures thereof.

According to one particularly preferred embodiment, the gelling agent is chosen from associative polymers.

For the purposes of the present invention, the term "associative polymer" means any amphiphilic polymer comprising in its structure at least one fatty chain and at least one hydrophilic portion. The associative polymers in accordance with the present invention may be anionic, cationic, nonionic or amphoteric.

Associative Anionic Polymers

Among the associative anionic polymers that may be mentioned are those comprising at least one hydrophilic unit, and at least one fatty-chain allyl ether unit, more particularly those whose hydrophilic unit is formed by an unsaturated ethylenic anionic monomer, advantageously by a vinylcarboxylic acid and most particularly by an acrylic acid or a methacrylic acid or mixtures thereof, and whose fatty-chain allyl ether unit corresponds to the monomer of formula (I) below:

$$CH_2=C(R')CH_2 \; O \; B_n \; R \qquad (I)$$

in which R' denotes H or $CH_3$, B denotes the ethylenoxy radical, n is zero or denotes an integer ranging from 1 to 100, R denotes a hydrocarbon-based radical chosen from alkyl, arylalkyl, aryl, alkylaryl and cycloalkyl radicals, comprising from 8 to 30 carbon atoms, preferably 10 to 24 and even more particularly from 12 to 18 carbon atoms.

Anionic amphiphilic polymers of this type are described and prepared, according to an emulsion polymerization process, in patent EP-0 216 479.

Among the associative anionic polymers that may also be mentioned are maleic anhydride/$C_{30}$-$C_{38}$ α-olefin/alkyl maleate terpolymers, such as the product (maleic anhydride/$C_{30}$-$C_{38}$ α-olefin/isopropyl maleate copolymer) sold under the name Performa V 1608 by the company Newphase Technologies.

Among the associative anionic polymers, it is possible, according to one preferred embodiment, to use copolymers comprising among their monomers an α,β-monoethylenically unsaturated carboxylic acid and an ester of an α,β-monoethylenically unsaturated carboxylic acid and of an oxyalkylenated fatty alcohol.

Preferentially, these compounds also comprise as monomer an ester of an α,β-monoethylenically unsaturated carboxylic acid and of a $C_1$-$C_4$ alcohol.

Examples of compounds of this type that may be mentioned include Aculyn 22® sold by the company Röhm & Haas, which is a methacrylic acid/ethyl acrylate/oxyalkylenated stearyl methacrylate (comprising 20 OE units) terpolymer or Aculyn 28 (methacrylic acid/ethyl acrylate/oxyethylenated behenyl methacrylate (25 OE) terpolymer).

Examples of associative anionic polymers that may also be mentioned include anionic polymers comprising at least one hydrophilic unit of unsaturated olefinic carboxylic acid type, and at least one hydrophobic unit exclusively of the type such as a ($C_{10}$-$C_{30}$) alkyl ester of an unsaturated carboxylic acid. Examples that may be mentioned include the anionic polymers described and prepared according to patents U.S. Pat. Nos. 3,915,921 and 4,509,949.

Cationic Associative Polymers

Cationic associative polymers that may be mentioned include quaternized cellulose derivatives and polyacrylates bearing amine side groups.

The quaternized cellulose derivatives are, in particular:

quaternized celluloses modified with groups comprising at least one fatty chain, such as alkyl, arylalkyl or alkylaryl groups comprising at least 8 carbon atoms, or mixtures thereof, quaternized hydroxyethylcelluloses modified with groups comprising at least one fatty chain, such as alkyl, arylalkyl or alkylaryl groups comprising at least 8 carbon atoms, or mixtures thereof.

The polyacrylates bearing quaternized or non-quaternized amine side groups contain, for example, hydrophobic groups of the type such as steareth-20 (polyoxyethylenated (20) stearyl alcohol).

The alkyl radicals borne by the above quaternized celluloses or hydroxyethylcelluloses preferably comprise from 8 to 30 carbon atoms. The aryl radicals preferably denote phenyl, benzyl, naphthyl or anthryl groups.

Examples of quaternized alkylhydroxyethylcelluloses containing $C_8$-$C_{30}$ fatty chains that may be indicated include the products Quatrisoft LM 200, Quatrisoft LM-X 529-18-A, Quatrisoft LM-X 529-18B ($C_{12}$ alkyl) and Quatrisoft LM-X 529-8 ($C_{18}$ alkyl) sold by the company Amerchol and the products Crodacel QM, Crodacel QL ($C_{12}$ alkyl) and Crodacel QS ($C_{18}$ alkyl) sold by the company Croda.

Examples of polyacrylates bearing amino side chains that may be mentioned are the polymers 8781-121B or 9492-103 from the company National Starch.

Nonionic Associative Polymers

The nonionic associative polymers may be chosen from:
celluloses modified with groups comprising at least one fatty chain, for instance hydroxyethylcelluloses modified with groups comprising at least one fatty chain, such as alkyl groups, especially of $C_8$-$C_{22}$, arylalkyl and alkylaryl groups, such as Natrosol Plus Grade 330 CS ($C_{16}$ alkyls) sold by the company Aqualon,
celluloses modified with alkylphenyl polyalkylene glycol ether groups, such as the product Amercell Polymer HM-1500 (nonylphenyl polyethylene glycol (15) ether) sold by the company Amerchol,
guars such as hydroxypropyl guar, modified with groups comprising at least one fatty chain such as an alkyl chain,
copolymers of vinylpyrrolidone and of fatty-chain hydrophobic monomers,
copolymers of $C_1$-$C_6$ alkyl methacrylates or acrylates and of amphiphilic monomers comprising at least one fatty chain,
copolymers of hydrophilic methacrylates or acrylates and of hydrophobic monomers comprising at least one fatty chain, for instance the polyethylene glycol methacrylate/lauryl methacrylate copolymer,
associative polyurethanes.

Associative polyurethanes are nonionic block copolymers comprising in the chain both hydrophilic blocks usually of polyoxyethylene nature (polyurethanes may also be referred to as polyurethane polyethers), and hydrophobic blocks that may be aliphatic sequences alone and/or cycloaliphatic and/or aromatic sequences.

In particular, these polymers comprise at least two hydrocarbon-based lipophilic chains containing from 6 to 30 carbon atoms, separated by a hydrophilic block, the hydrocarbon-based chains possibly being pendent chains or chains at the end of the hydrophilic block. In particular, it is possible for one or more pendent chains to be included. In addition, the polymer may comprise a hydrocarbon-based chain at one end or at both ends of a hydrophilic block.

Associative polyurethanes may be block polymers, in triblock or multiblock form. The hydrophobic blocks may thus be at each end of the chain (for example: triblock copolymer containing a hydrophilic central block) or distributed both at the ends and in the chain (for example: multiblock copolymer). These polymers may also be graft polymers or star polymers. Preferably, the associative polyurethanes are triblock copolymers in which the hydrophilic block is a polyoxyethylene chain comprising from 50 to 1000 oxyethylene groups. In general, associative polyurethanes comprise a urethane bond between the hydrophilic blocks, whence arises the name.

According to one preferred embodiment, a nonionic associative polymer of polyurethane polyether type is used as gelling agent. By way of example of polyurethane polyethers that may not be used in the invention, mention may be made of the polymer $C_{16}$-$OE_{120}$-$C_{16}$ from the company Servo Delden (under the name SER AD FX1100, which is a molecule containing a urethane function and having a weight-average molecular weight of 1300), OE being an oxyethylene unit.

RHEOLATE 205 bearing a urea function, sold by the company Rheox, or RHEOLATE 208 or 204, or alternatively RHEOLATE FX 1100 by Elementis of INCI name Steareth-100/PEG-136/HDI, may also be used as associative polyurethane polymer. These associative polyurethanes are sold in pure form. The product DW 1206B from Röhm & Haas containing a $C_{20}$ alkyl chain and a urethane bond, sold at a solids content of 20% in water, may also be used.

It is also possible to use solutions or dispersions of these polymers, especially in water or in aqueous-alcoholic medium. Examples of such polymers that may be mentioned include SER AD FX1010, SER AD FX1035 and SER AD 1070 from the company Servo Delden, and RHEOLATE 255, RHEOLATE 278 and RHEOLATE 244 sold by the company Rheox. It is also possible to use the products ACULYN 46, DW 1206F and DW 1206J, and also ACRYSOL RM 184 or ACRYSOL 44 from the company Röhm & Haas, or alternatively BORCHIGEL LW 44 from the company Borchers, and mixtures thereof.

According to one preferred embodiment, the hydrophilic gelling agent is chosen from:
optionally modified hydroxypropyl guar, in particular hydroxypropyl guar modified with sodium methylcarboxylate groups (Jaguar XC97-1, Rhodia) or hydroxypropyltrimethylammonium guar chloride,
vinyl polymers, such as polyvinyl alcohol,
anionic associative polymers derived from (meth)acrylic acid, such as the non-crosslinked copolymer obtained from methacrylic acid and steareth-20 methacrylate, sold under the name ACULYN 22 by Röhm & Haas,
nonionic associative polymers of polyurethane polyether type, such as Steareth-100/PEG-136/HDI Copolymer sold under the name RHEOLATE FX 1100 by Elementis.

According to one preferred embodiment, the hydrophilic gelling agent is chosen from:
optionally modified hydroxypropyl guar, in particular hydroxypropyl guar modified with sodium methyl carboxylate groups (Jaguar XC97-1, Rhodia) or hydroxypropyltrimethylammonium guar chloride,
anionic associative polymers derived from (meth)acrylic acid, such as the non-crosslinked copolymer obtained from methacrylic acid and steareth-20 methacrylate, sold under the name ACULYN 22 by Röhm & Haas,
nonionic associative polymers of polyurethane polyether type, such as Steareth-100/PEG-136/HDI Copolymer sold under the name RHEOLATE FX 1100 by Elementis.

Amphoteric Associative Polymers

Among the associative amphoteric polymers of the invention, mention may be made of crosslinked or non-crosslinked, branched or unbranched amphoteric polymers, which may be obtained by copolymerization 1) of at least one monomer of formula (IVa) or (IVb):

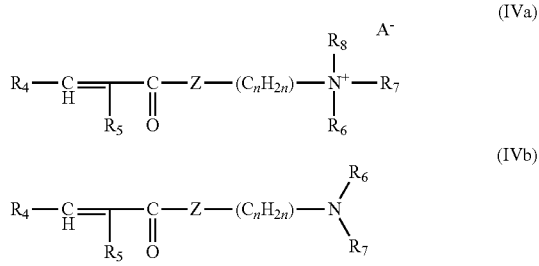

in which $R_4$ and $R_5$, which may be identical or different, represent a hydrogen atom or a methyl radical, $R_6$, $R_7$ and $R_8$, which may be identical or different, represent a linear or branched alkyl radical containing from 1 to 30 carbon atoms, Z represents a group NH or an oxygen atom, n is an integer from 2 to 5, $A^-$ denotes an anion derived from a mineral or organic acid, such as a methosulfate anion or a halide such as chloride or bromide.

in which $R_9$ and $R_{10}$, which may be identical or different, represent a hydrogen atom or a methyl radical;

$Z_1$ represents a group OH or a group $NHC(CH_3)_2CH_2SO_3H$;

3) of at least one monomer of formula (VI):

in which $R_9$ and $R_{10}$, which may be identical or different, represent a hydrogen atom or a methyl radical, X denotes an oxygen or nitrogen atom and $R_{11}$ denotes a linear or branched alkyl radical containing from 1 to 30 carbon atoms;

4) optionally at least one crosslinking or branching agent; at least one of the monomers of formula (IVa), (IVb) or (VI) comprising at least one fatty chain containing from 8 to 30 carbon atoms and the said compounds of the monomers of formulae (IVa), (IVb), (V) and (VI) possibly being quaternized, for example with a $C_1$-$C_4$ alkyl halide or a $C_1$-$C_4$ dialkyl sulfate.

The monomers of formulae (IVa) and (IVb) of the present invention are preferably chosen from the group formed by:
dimethylaminoethyl methacrylate, dimethylaminoethyl acrylate,
diethylaminoethyl methacrylate, diethylaminoethyl acrylate,
dimethylaminopropyl methacrylate, dimethylaminopropyl acrylate,
dimethylaminopropylmethacrylamide or dimethylaminopropylacrylamide, optionally quaternized, for example with a $C_1$-$C_4$ alkyl halide or a $C_1$-$C_4$ dialkyl sulfate.

More particularly, the monomer of formula (IVa) is chosen from acrylamidopropyltrimethylammonium chloride and methacrylamidopropyl trimethylammonium chloride.

The compounds of formula (V) of the present invention are preferably chosen from the group formed by acrylic acid, methacrylic acid, crotonic acid, 2-methylcrotonic acid, 2-acrylamido-2-methylpropanesulfonic acid and 2-methacrylamido-2-methylpropanesulfonic acid. More particularly, the monomer of formula (V) is acrylic acid.

The monomers of formula (VI) of the present invention are preferably chosen from the group formed by $C_{12}$-$C_{22}$ and more particularly $C_{16}$-$C_{18}$ alkyl acrylates or methacrylates.

The crosslinking or branching agent is preferably chosen from N,N'-methylenebisacrylamide, triallylmethylammonium chloride, allyl methacrylate, n-methylolacrylamide, polyethylene glycol dimethacrylates, ethylene glycol dimethacrylate, diethylene glycol dimethacrylate, 1,6-hexanediol dimethacrylate and allyl sucrose.

The polymers according to the invention may also contain other monomers such as nonionic monomers and in particular $C_1$-$C_4$ alkyl acrylates or methacrylates.

The ratio of the number of cationic charges/anionic charges in these amphoteric polymers is preferably equal to about 1.

The weight-average molecular weights of the associative amphoteric polymers represents a weight-average molecular mass of greater than 500 g/mol, preferably between 10 000 g/mol and 10 000 000 g/mol and even more preferentially between 100 000 g/mol and 8 000 000 g/mol.

Preferably, the associative amphoteric polymers of the invention contain from 1 mol % to 99 mol %, more preferentially from 20 mol % to 95 mol % and even more preferentially from 25 mol % to 75 mol % of compound(s) of formula (IVa) or (IVb). They also preferably contain from 1 mol % to 80 mol %, more preferentially from 5 mol % to 80 mol % and even more preferentially from 25 mol % to 75 mol % of compound(s) of formula (V). The content of compound(s) of formula (VI) is preferably between 0.1 mol % and 70 mol %, more preferentially between 1 mol % and 50 mol % and even more preferentially between 1 mol % and 10 mol %. The crosslinking or branching agent, when it is present, is preferably between 0.0001 mol % and 1 mol % and even more preferentially between 0.0001 mol % and 0.1 mol %.

Preferably, the mole ratio between the compound(s) of formula (IVa) or (IVb) and the compound(s) of formula (V) ranges from 20/80 to 95/5 and more preferentially from 25/75 to 75/25.

The associative amphoteric polymers according to the invention are described, for example, in patent application WO 98/44012.

The amphoteric polymers that are particularly preferred according to the invention are chosen from acrylic acid/acrylamidopropyltrimethylammonium chloride/stearyl methacrylate copolymers.

According to one preferred embodiment, the hydrophilic gelling agent is chosen from:
clays;
optionally modified polymers of natural origin, such as xanthan gum;
AMPS/acrylamide copolymers such as a copolymer of INCI name Polyacrylamide (and) C13-14 Isoparaffin Laureth-7, such as Sepigel;
nonionic associative polymers of polyurethane polyether type, such as a copolymer of INCI name Steareth-100/PEG-136/HDI;
and mixtures thereof.

The hydrophilic gelling agent(s) may be present in the composition according to the invention in a solids content of greater than or equal to 0.1% by weight relative to the total weight of the composition. In particular, the hydrophilic gelling agent(s) may be present in the composition according to the invention in a solids content ranging from 0.5% to 5% by weight and preferably from 1% to 3% by weight relative to the total weight of the composition.

Fatty Phase

A cosmetic composition according to the invention advantageously comprises at least one fatty phase as binder.

This fatty phase is preferably liquid. It preferably comprises at least one oil, preferably a hydrocarbon-based oil.

The term "oil" means a water-immiscible non-aqueous compound that is liquid at room temperature (25° C.) and at atmospheric pressure (760 mmHg).

This fatty phase may in particular comprise at least one non-volatile oil and/or one volatile oil. Preferably, this fatty phase comprises at least one non-volatile oil, preferably a hydrocarbon-based oil. Preferably, the composition according to the invention is free of volatile oil.

The content of oil in the said composition may range from 0.5% to 30% by weight, in particular from 5% to 20% by weight and better still from 8% to 15% by weight relative to the total weight of the composition.

Non-Volatile Oil

The term "non-volatile oil" means an oil that remains on the skin or the keratin fibre at room temperature and pressure. More precisely, a non-volatile oil has an evaporation rate strictly less than 0.01 mg/cm$^2$/min.

This non-volatile oil may be a hydrocarbon-based, silicone or fluoro oil. It is preferably a hydrocarbon-based oil.

Non-volatile oils that may especially be mentioned include:
- hydrocarbon-based oils of animal origin,
- hydrocarbon-based oils of plant origin, such as phytostearyl esters, such as phytostearyl oleate, phytostearyl isostearate and lauroyl/octyldodecyl/phytostearyl glutamate; triglycerides formed from fatty acid esters of glycerol, in particular whose fatty acids may have chain lengths ranging from $C_4$ to $C_{36}$ and especially from $C_{18}$ to $C_{36}$, these oils possibly being linear or branched, and saturated or unsaturated; these oils may especially be heptanoic or octanoic triglycerides, shea oil, alfalfa oil, poppy oil, pumpkin oil, millet oil, barley oil, quinoa oil, rye oil, candlenut oil, passionflower oil, shea butter oil, aloe oil, sweet almond oil, peach stone oil, groundnut oil, argan oil, avocado oil, baobab oil, borage oil, broccoli oil, calendula oil, camellina oil, carrot oil, safflower oil, hemp oil, rapeseed oil, cottonseed oil, coconut oil, marrow seed oil, wheatgerm oil, jojoba oil, lily oil, macadamia oil, corn oil, meadowfoam oil, St-John's wort oil, monoi oil, hazelnut oil, apricot kernel oil, walnut oil, olive oil, evening primrose oil, palm oil, blackcurrant pip oil, kiwi seed oil, grape seed oil, pistachio oil, pumpkin oil, quinoa oil, musk rose oil, sesame oil, soybean oil, sunflower oil, castor oil and watermelon oil, and mixtures thereof, or alternatively caprylic/capric acid triglycerides, such as those sold by the company Stèarineries Dubois or those sold under the names Miglyol 810®, 812® and 818® by the company Dynamit Nobel,
- synthetic ethers containing from 10 to 40 carbon atoms;
- synthetic esters, for instance the oils of formula $R_1COOR_2$, in which $R_1$ represents at least one linear or branched fatty acid residue containing from 1 to 40 carbon atoms and $R_2$ represents a hydrocarbon-based chain, which is especially branched, containing from 1 to 40 carbon atoms, on condition that $R_1+R_2 \geq 10$. The esters may be chosen especially from fatty acid esters of alcohols, for instance cetostearyl octanoate, isopropyl alcohol esters, such as isopropyl myristate, isopropyl palmitate, ethyl palmitate, 2-ethylhexyl palmitate, isopropyl stearate, isopropyl isostearate, isostearyl isostearate, octyl stearate, hydroxylated esters, for instance isostearyl lactate, octyl hydroxystearate, diisopropyl adipate, heptanoates, and especially isostearyl heptanoate, alcohol or polyalcohol octanoates, decanoates or ricinoleates, for instance propylene glycol dioctanoate, cetyl octanoate, tridecyl octanoate, 2-ethylhexyl 4-diheptanoate, 2-ethylhexyl palmitate, alkyl benzoates, polyethylene glycol diheptanoate, propylene glycol 2-diethylhexanoate, and mixtures thereof, $C_{12}$-$C_{15}$ alcohol benzoates, hexyl laurate, neopentanoic acid esters, for instance isodecyl neopentanoate, isotridecyl neopentanoate, isostearyl neopentanoate, octyldodecyl neopentanoate, isononanoic acid esters, for instance isononyl isononanoate, isotri decyl isononanoate, octyl isononanoate, hydroxylated esters, for instance isostearyl lactate and diisostearyl malate,
- polyol esters and pentaerythritol esters, for instance dipentaerythritol tetrahydroxystearate/tetraisostearate,
- esters of diol dimers and of diacid dimers,
- copolymers of diol dimer and of diacid dimer and esters thereof, such as dilinoleyl diol dimer/dilinoleic dimer copolymers, and esters thereof,
- copolymers of polyols and of diacid dimers, and esters thereof,
- fatty alcohols that are liquid at room temperature, with a branched and/or unsaturated carbon-based chain containing from 12 to 26 carbon atoms, for instance 2-octyldodecanol, isostearyl alcohol, oleyl alcohol, 2-hexyldecanol, 2-butyloctanol and 2-undecylpentadecanol,
- $C_{12}$-$C_{22}$ higher fatty acids, such as oleic acid, linoleic acid and linolenic acid, and mixtures thereof;
- dialkyl carbonates, the two alkyl chains possibly being identical or different, such as dicaprylyl carbonate;
- oils with a molar mass of between about 400 and about 10 000 g/mol, in particular about 650 to about 10 000 g/mol, in particular from about 750 to about 7500 g/mol and more particularly ranging from about 1000 to about 5000 g/mol; mention may be made especially, alone or as a mixture, of (i) lipophilic polymers such as polybutylenes, polyisobutylenes, for example hydrogenated, polydecenes and hydrogenated polydecenes, vinylpyrrolidone copolymers, such as the vinylpyrrolidone/1-hexadecene copolymer, and polyvinylpyrrolidone (PVP) copolymers, such as the copolymers of a $C_2$-$C_{30}$ alkene, such as $C_3$-$C_{22}$, and combinations thereof; (ii) linear fatty acid esters containing a total carbon number ranging from 35 to 70, for instance pentaerythrityl tetrapelargonate; (iii) hydroxylated esters such as polyglyceryl-2 triisostearate; (iv) aromatic esters such as tridecyl trimellitate; (v) esters of fatty alcohols or of branched $C_{24}$-$C_{28}$ fatty acids, such as those described in patent U.S. Pat. No. 6,491,927 and pentaerythritol esters, and especially triisoarachidyl citrate, pentaerythrityl tetraisononanoate, glyceryl triisostearate, glyceryl 2-tridecyltetradecanoate, pentaerythrityl tetraisostearate, poly(2-glyceryl) tetraisostearate or pentaerythrityl 2-tetradecyltetradecanoate; (vi) diol dimer esters and polyesters, such as esters of diol dimer and of fatty acid, and esters of diol dimer and of diacid.

Preferably, the composition according to the invention comprises a non-volatile oil of plant origin, a polyol ester and a particular synthetic ester. Preferably, this non-volatile oil of animal origin is a caprylic/capric acid triglyceride. Preferably, this polyol ester is dipentaerythrityl tetrahydroxystearate/tetraisostearate. Preferably, this particular synthetic ester is stearyl octyldodecyl stearate.

As will be seen hereinafter, besides a non-volatile oil serving as binder for the pulverulent phase, a non-volatile oil, which is preferably different, may serve as solvent for at least one organopolysiloxane elastomer according to the invention. According to one preferred embodiment, at least one non-volatile oil serving as binder for the pulverulent phase is hydrocarbon-based, whereas, where appropriate, at least one non-volatile oil containing the said organopolysiloxane elastomer is a silicone oil.

Volatile Oil

The term "volatile oil" means an oil (or non-aqueous medium) that can evaporate on contact with the skin in less than one hour, at room temperature and atmospheric pressure. The volatile oil is a cosmetic volatile oil, which is liquid at room temperature. More specifically, a volatile oil has an evaporation rate of between 0.01 and 200 mg/cm$^2$/min, limits inclusive.

To measure this evaporation rate, 15 g of oil or of oil mixture to be tested are placed in a crystallizing dish 7 cm in diameter, placed on a balance that is in a large temperature-regulated chamber of about 0.3 m$^3$, at a temperature of 25° C., and hygrometry-regulated, at a relative humidity of 50%. The liquid is allowed to evaporate freely, without stirring it, while providing ventilation by means of a fan (Papst-Motoren, reference 8550 N, rotating at 2700 rpm) placed in a vertical position above the crystallizing dish containing the said oil or the said mixture, the blades being directed towards the crystallizing dish, 20 cm away from the bottom of the crystallizing dish. The mass of oil remaining in the crystallizing dish is measured at regular intervals. The evaporation rates are expressed in mg of oil evaporated per unit area (cm$^2$) and per unit of time (minutes).

This volatile oil may be a hydrocarbon-based oil, silicone oil or fluoro oil. It is preferably a hydrocarbon-based oil.

The term "hydrocarbon-based oil" means an oil mainly containing hydrogen and carbon atoms.

The term "silicone oil" means an oil containing at least one silicon atom, and especially containing Si—O groups. According to one embodiment, the said composition comprises less than 10% by weight of non-volatile silicone oil(s), relative to the total weight of the composition, better still less than 5% by weight, or even is free of silicone oil.

The term "fluoro oil" means an oil comprising at least one fluorine atom.

The oils may optionally comprise oxygen, nitrogen, sulfur and/or phosphorus atoms, for example in the form of hydroxyl or acid radicals.

The volatile oils may be chosen from hydrocarbon-based oils containing from 8 to 16 carbon atoms, and especially $C_8$-$C_{16}$ branched alkanes (also known as isoparaffins), for instance isododecane, isodecane and isohexadecane.

The volatile hydrocarbon-based oil may also be a linear volatile alkane containing 7 to 17 carbon atoms, in particular 9 to 15 carbon atoms and more particularly 11 to 13 carbon atoms. Mention may be made especially of n-nonadecane, n-decane, n-undecane, n-dodecane, n-tridecane, n-tetradecane, n-pentadecane and n-hexadecane, and mixtures thereof.

Organopolysiloxane Elastomers

A composition according to the invention comprises an organopolysiloxane elastomer. This elastomer may serve as fatty-phase gelling agent.

These particular elastomers, when combined with the pulverulent phase that is moreover required according to the invention, make it possible to obtain softness and comfort properties (suppleness of the deposit) for the deposits formed on the skin from compositions comprising them.

The term "organopolysiloxane elastomer" means a supple, deformable organopolysiloxane with viscoelastic properties and especially the consistency of a sponge or a supple sphere. Its modulus of elasticity is such that this material withstands deformation and has limited stretchability and contractability. This material is capable of regaining its original shape after stretching.

The organopolysiloxane elastomer in accordance with the invention is preferably crosslinked. Preferably, this elastomer is non-cyclic. According to one preferred embodiment, organopolysiloxane elastomers having the INCI name dimethicone/vinyl dimethicone copolymer are used.

A composition according to the invention preferably comprises at least one organopolysiloxane elastomer conveyed in at least one hydrocarbon-based oil and/or silicone oil, which is preferably non-volatile. Preferably, the said composition comprises at least one organopolysiloxane elastomer conveyed in at least one non-volatile silicone oil having the INCI name dimethicone.

Non-Emulsifying Organopolysiloxane Elastomers

Thus, the organopolysiloxane elastomer may be obtained by crosslinking addition reaction of diorganopolysiloxane containing at least one hydrogen bonded to silicon and of diorganopolysiloxane containing ethylenically unsaturated groups bonded to silicon, especially in the presence of a platinum catalyst; or by dehydrogenation crosslinking condensation reaction between a diorganopolysiloxane containing hydroxyl end groups and a diorganopolysiloxane containing at least one hydrogen bonded to silicon, especially in the presence of an organotin; or by crosslinking condensation reaction of a diorganopolysiloxane containing hydroxyl end groups and of a hydrolyzable organopolysilane; or by thermal crosslinking of organopolysiloxane, especially in the presence of an organoperoxide catalyst; or by crosslinking of organopolysiloxane via high-energy radiation such as gamma rays, ultraviolet rays or an electron beam.

Preferably, the organopolysiloxane elastomer is obtained by crosslinking addition reaction (A) of diorganopolysiloxane containing at least two hydrogens each bonded to a silicon, and (B) of diorganopolysiloxane containing at least two ethylenically unsaturated groups bonded to silicon, especially in the presence (C) of a platinum catalyst.

In particular, the organopolysiloxane elastomer may be obtained by reaction of a dimethylpolysiloxane with dimethylvinylsiloxy end groups and of methylhydrogenopolysiloxane with trimethylsiloxy end groups, in the presence of a platinum catalyst.

Compound (A) is the base compound for the formation of organopolysiloxane elastomer, and the crosslinking is performed by addition reaction of compound (A) with compound (B) in the presence of the catalyst (C).

Compound (A) is in particular an organopolysiloxane containing at least two hydrogen atoms bonded to different silicon atoms in each molecule.

Compound (A) may have any molecular structure, especially a linear-chain or branched-chain structure or a cyclic structure.

Compound (A) may have a viscosity at 25° C. ranging from 1 to 50 000 centistokes, especially so as to be miscible with compound (B).

The organic groups bonded to the silicon atoms of compound (A) may be alkyl groups such as methyl, ethyl, propyl, butyl, octyl; substituted alkyl groups such as 2-phenylethyl, 2-phenylpropyl or 3,3,3-trifluoropropyl; aryl groups such as phenyl, tolyl, xylyl; substituted aryl groups such as phenylethyl; and substituted monovalent hydrocarbon-based groups such as an epoxy group, a carboxylate ester group or a mercapto group.

Compound (A) may thus be chosen from methylhydrogenopolysiloxanes containing trimethylsiloxy end groups, dimethyl siloxane-methylhydrogenosiloxane copolymers containing trimethylsiloxy end groups, and dimethylsiloxane-methylhydrogenosiloxane cyclic copolymers.

Compound (B) is advantageously a diorganopolysiloxane containing at least two lower alkenyl groups (for example $C_2$-$C_4$); the lower alkenyl group may be chosen from vinyl, allyl and propenyl groups. These lower alkenyl groups may be located in any position of the organopolysiloxane molecule, but are preferably located at the ends of the organopolysiloxane molecule. The organopolysiloxane (B) may have a branched-chain, linear-chain, cyclic or network structure, but the linear-chain structure is preferred. Compound (B) may have a viscosity ranging from the liquid state to the gum state. Preferably, compound (B) has a viscosity of at least 100 centistokes at 25° C.

Besides the abovementioned alkenyl groups, the other organic groups bonded to the silicon atoms in compound (B) may be alkyl groups such as methyl, ethyl, propyl, butyl or octyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group.

The organopolysiloxanes (B) may be chosen from methylvinylpolysiloxanes, methylvinylsiloxane-dimethylsiloxane copolymers, dimethylpolysiloxanes containing dimethylvinylsiloxy end groups, dimethylsiloxane-methylphenylsiloxane copolymers containing dimethylvinylsiloxy end groups, dimethylsiloxane-diphenylsiloxane-methylvinylsiloxane copolymers containing dimethylvinylsiloxy end groups, dimethylsiloxane-methylvinylsiloxane copolymers containing trimethylsiloxy end groups, dimethylsiloxane-methylphenyl siloxane-methyl vinyl siloxane copolymers containing trimethylsiloxy end groups, methyl(3,3,3-trifluoropropyl)polysiloxanes containing dimethylvinylsiloxy end groups, and dimethylsiloxane-methyl(3,3,3-trifluoropropyl)siloxane copolymers containing dimethylvinylsiloxy end groups.

In particular, the organopolysiloxane elastomer may be obtained by reaction of a dimethyl polysiloxane containing dimethylvinylsiloxy end groups and of methylhydrogenopolysiloxane containing trimethylsiloxy end groups, in the presence of a platinum catalyst.

Advantageously, the sum of the number of ethylenic groups per molecule in compound (B) and of the number of hydrogen atoms bonded to silicon atoms per molecule in compound (A) is at least 5.

It is advantageous for compound (A) to be added in an amount such that the molecular ratio between the total amount of hydrogen atoms bonded to silicon atoms in compound (A) and the total amount of all the ethylenically unsaturated groups in compound (B) is within the range from 1.5/1 to 20/1.

Compound (C) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

The catalyst (C) is preferably added in an amount of from 0.1 to 1000 parts by weight and better still from 1 to 100 parts by weight, as clean platinum metal, per 1000 parts by weight of the total amount of compounds (A) and (B).

The elastomer is advantageously a non-emulsifying elastomer.

The term "non-emulsifying" defines organopolysiloxane elastomers not containing any hydrophilic chains, and in particular not containing any polyoxyalkylene units (especially polyoxyethylene or polyoxypropylene) or any polyglyceryl units.

The organopolysiloxane elastomer particles are preferably conveyed in the form of a gel formed from an elastomeric organopolysiloxane included in at least one hydrocarbon-based oil and/or one silicone oil. In these gels, the organopolysiloxane particles may be spherical or non-spherical particles.

Spherical non-emulsifying elastomers that may be used include, for example, those sold under the names DC 9040, DC 9041, DC 9509, DC 9505 by the company Dow Corning.

Mention may also be made of those sold under the names KSG-6, KSG-15, KSG-16, KSG-18, KSG-41, KSG-42, KSG-43 and KSG-44 by the company Shin-Etsu; Gransil SR 5CYC Gel, Gransil SR DMF 10 Gel and Gransil SR DC556 Gel from the company Gransil RPS from Grant Industries; 1229-02-167, 1229-02-168 and SFE 839 from the company General Electric.

According to one particular embodiment, elastomers may be used as a mixture with a cyclic silicone oil. An example that may be mentioned is the mixture of crosslinked organopolysiloxane/cyclopentasiloxane or a mixture of crosslinked organopolysiloxane/cyclohexasiloxane, for instance Gransil RPS D5 or Gransil RPS D6 from the company Grant Industries.

Emulsifying Organopolysiloxane Elastomers

The term "emulsifying organopolysiloxane elastomer" means an organopolysiloxane elastomer comprising at least one hydrophilic chain, such as polyoxyalkylenated organopolysiloxane elastomers and polyglycerolated silicone elastomers.

The emulsifying organopolysiloxane elastomer may be chosen from polyoxyalkylenated organopolysiloxane elastomers.

The polyoxyalkylenated organopolysiloxane elastomer is a crosslinked organopolysiloxane elastomer that may be obtained by crosslinking addition reaction of diorganopolysiloxane containing at least one hydrogen bonded to silicon and of a polyoxyalkylene containing at least two ethylenically unsaturated groups.

Preferably, the organopolysiloxane elastomer is obtained by crosslinking addition reaction (A1) of diorganopolysiloxane containing at least two hydrogens each bonded to a silicon, and (B1) of polyoxyalkylene containing at least two ethylenically unsaturated groups, especially in the presence (C1) of a platinum catalyst, as described, for instance, in patents U.S. Pat. Nos. 5,236,986 and 5,412,004.

In particular, the organopolysiloxane may be obtained by reaction of polyoxyalkylene (especially polyoxyethylene and/or polyoxypropylene) with dimethylvinylsiloxy end groups and of methylhydrogenopolysiloxane with trimethylsiloxy end groups, in the presence of a platinum catalyst.

The organic groups bonded to the silicon atoms of compound (A1) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenylethyl; and substituted monovalent hydrocarbon-based groups such as an epoxy group, a carboxylate ester group or a mercapto group.

Compound (A1) may thus be chosen from methylhydrogenopolysiloxanes containing trimethylsiloxy end groups, dimethylsiloxane-methylhydrogenosiloxane copolymers containing trimethylsiloxy end groups, dimethylsiloxane-methylhydrogenosiloxane cyclic copolymers, dimethyl siloxane-methylhydrogenosiloxane-laurylmethylsiloxane copolymers containing trimethylsiloxy end groups.

Compound (C1) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

Advantageously, the polyoxyalkylenated organopolysiloxane elastomers may be formed from divinyl compounds, in particular polyoxyalkylenes containing at least two vinyl groups, which react with Si—H bonds of a polysiloxane.

Polyoxyalkylenated elastomers are especially described in patents U.S. Pat. Nos. 5,236,986, 5,412,004, 5,837,793 and 5,811,487, the content of which is incorporated by reference.

Polyoxyalkylenated organopolysiloxane elastomers that may be used include those sold under the names KSG-21, KSG-20, KSG-30, KSG-31, KSG-32, KSG-33, KSG-210, KSG-310, KSG-320, KSG-330 and KSG-340 by the company Shin-Etsu, and DC9010 and DC9011 by the company Dow Corning.

The emulsifying organopolysiloxane elastomer may also be chosen from polyglycerolated organopolysiloxane elastomers.

The polyglycerolated organopolysiloxane elastomer according to the invention is an organopolysiloxane elastomer that may be obtained by crosslinking addition reaction of diorganopolysiloxane containing at least one hydrogen bonded to silicon and of polyglycerolated compounds containing ethylenically unsaturated groups, especially in the presence of a platinum catalyst.

Preferably, the organopolysiloxane elastomer is obtained by crosslinking addition reaction (A2) of diorganopolysiloxane containing at least two hydrogens each bonded to a silicon, and (B2) of glycerolated compounds containing at least two ethylenically unsaturated groups, especially in the presence (C2) of a platinum catalyst.

In particular, the organopolysiloxane may be obtained by reaction of a polyglycerolated compound with dimethylvinylsiloxy end groups and of methylhydrogenopolysiloxane with trimethylsiloxy end groups, in the presence of a platinum catalyst.

Compound (A2) is the base reagent for the formation of an organopolysiloxane elastomer, and the crosslinking is performed by addition reaction of compound (A2) with compound (B2) in the presence of the catalyst (C2).

Compound (A2) is in particular an organopolysiloxane containing at least two hydrogen atoms bonded to different silicon atoms in each molecule.

Compound (A2) may have any molecular structure, especially a linear-chain or branched-chain structure or a cyclic structure.

Compound (A2) may have a viscosity at 25° C. ranging from 1 to 50 000 centistokes, especially so as to be miscible with compound (B2).

The organic groups bonded to the silicon atoms in compound (A2) may be alkyl groups containing from 1 to 18 carbon atoms, such as methyl, ethyl, propyl, butyl, octyl, decyl, dodecyl (or lauryl), myristyl, cetyl or stearyl; substituted alkyl groups such as 2-phenylethyl, 2-phenylpropyl or 3,3,3-trifluoropropyl; aryl groups such as phenyl, tolyl or xylyl; substituted aryl groups such as phenylethyl; and substituted monovalent hydrocarbon-based groups such as an epoxy group, a carboxylate ester group or a mercapto group. Preferably, the said organic group is chosen from methyl, phenyl and lauryl groups.

Compound (A2) may thus be chosen from methylhydrogenopolysiloxanes containing trimethylsiloxy end groups, dimethylsiloxane-methylhydrogenosiloxane copolymers containing trimethylsiloxy end groups, dimethylsiloxane-methylhydrogenosiloxane cyclic copolymers and dimethylsiloxane-methylhydrogenosiloxane-laurylmethylsiloxane copolymers containing trimethylsiloxy end groups.

Compound (B2) may be a polyglycerolated compound corresponding to formula (B') below:

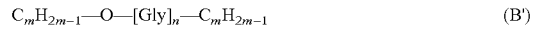

$$C_mH_{2m-1}\text{—O—}[Gly]_n\text{—}C_mH_{2m-1} \quad (B')$$

in which m is an integer ranging from 2 to 6, n is an integer ranging from 2 to 200, preferably ranging from 2 to 100, preferably ranging from 2 to 50, preferably ranging from 2 to 20, preferably ranging from 2 to 10 and preferentially ranging from 2 to 5, and in particular n is equal to 3; Gly denotes:

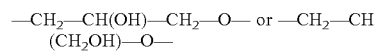

—CH$_2$—CH(OH)—CH$_2$—O— or —CH$_2$—CH(CH$_2$OH)—O—

Advantageously, the sum of the number of ethylenic groups per molecule in compound (B2) and of the number of hydrogen atoms bonded to silicon atoms per molecule in compound (A2) is at least 4.

It is advantageous for compound (A2) to be added in an amount such that the molecular ratio between the total amount of hydrogen atoms bonded to silicon atoms in compound (A2) and the total amount of all the ethylenically unsaturated groups in compound (B2) is within the range from 1/1 to 20/1.

Compound (C2) is the catalyst for the crosslinking reaction, and is especially chloroplatinic acid, chloroplatinic acid-olefin complexes, chloroplatinic acid-alkenylsiloxane complexes, chloroplatinic acid-diketone complexes, platinum black and platinum on a support.

The catalyst (C2) is preferably added in an amount of from 0.1 to 1000 parts by weight and better still from 1 to 100 parts by weight, as clean platinum metal, per 1000 parts by weight of the total amount of compounds (A2) and (B2).

The polyglycerolated organopolysiloxane elastomer is conveyed in gel form in at least one hydrocarbon-based oil and/or one silicone oil. In these gels, the polyglycerolated elastomer is often in the form of nonspherical particles.

Polyglycerolated organopolysiloxane elastomers that may be used include those sold under the names KSG-710, KSG-810, KSG-820, KSG-830 and KSG-840 by the company Shin-Etsu.

Advantageously, the organopolysiloxane elastomer under consideration according to the invention is chosen from spherical non-emulsifying organopolysiloxane elastomers, polyglycerolated organopolysiloxane elastomers and polyoxyalkylenated organopolysiloxane elastomers.

Advantageously, the organopolysiloxane elastomer under consideration according to the invention is chosen from spherical, preferably non-emulsifying organopolysiloxane elastomers.

Preferably, the organopolysiloxane elastomer is non-emulsifying, for example in the case of eyeshadow compositions, and in particular in the case of anhydrous compositions.

Preferably, the emulsifying system according to the invention does not comprise any emulsifying organopolysiloxane elastomer.

Even more preferably, the composition comprises an organopolysiloxane elastomer conveyed in a non-volatile oil combined with at least one organopolysiloxane elastomer in powder form. Such a combination may make it possible to increase the percentage of elastomer solids within the said non-volatile oil, to better control its viscosity and to limit the content to be incorporated into the said composition in order, if necessary, to make space for other compounds such as colouring agents and in particular nacres.

Such non-emulsifying elastomers in powder form especially comprise those sold under the names DC 9506 or DC 9701 by the company Dow Corning.

Preferably, the composition comprises an organopolysiloxane elastomer chosen from the product sold under the name DC 9041 by the company Dow Corning, KSG-16 by the company Shin-Etsu and DC 9701 by the company Dow Corning, and a mixture thereof. Even more preferentially, the composition comprises at least one organopolysiloxane elastomer chosen from the product sold under the name DC 9041 by the company Dow Corning and KSG-16 by the company Shin-Etsu, in combination with an organopolysiloxane elastomer sold under the name DC 9701 by the company Dow Corning.

Advantageously, the composition according to the invention comprises at least one organopolysiloxane elastomer, alone or as a mixture, in a solids content ranging from 0.2% to 8% by weight, preferably from 0.5% to 6% by weight and even more preferably from 1.5% to 3% by weight, and more preferentially ranging from 2% to 3% by weight, relative to the total weight of the composition, for example about 2% by weight.

The organopolysiloxane elastomer may be present in a ratio such that the mass proportion of organopolysiloxane elastomer relative to the pulverulent phase is between 0.05 and 0.35, preferably from 0.10 to 0.20 and even more preferably from 0.10 to 0.12.

Emulsifying System

The composition according to the invention comprises an emulsifying system. Such a composition comprises one or more surfactants. These surfactants may be present in a content ranging from 0.1% to 20% by weight relative to the total weight of the composition, advantageously from 0.5% to 15% by weight, preferably ranging from 1% to 10% by weight and in particular from 1.5% to 5% by weight, relative to the total weight of the composition.

An emulsifying surfactant appropriately chosen to obtain an oil-in-water emulsion is generally used. In particular, an emulsifying surfactant having at 25° C. an HLB balance (hydrophilic-lipophilic balance) within the Griffin sense of greater than or equal to 8 may be used.

The Griffin HLB value is defined in J. Soc. Cosm. Chem. 1954 (volume 5), pages 249-256.

These surfactants may be chosen from nonionic, anionic, cationic and amphoteric surfactants, and mixtures thereof.

Reference may be made to Kirk-Othmer's *Encyclopedia of Chemical Technology*, Volume 22, pp. 333-432, 3rd Edition, 1979, Wiley, for the definition of the emulsifying properties and functions of surfactants, in particular pp. 347-377 of this reference, for the anionic, amphoteric and nonionic surfactants.

The surfactants preferentially used in the composition according to the invention are chosen from:

a) nonionic surfactants with an FMB of less than 8 at 25° C., as mentioned above, for instance:

saccharide esters and ethers such as sucrose stearate, sucrose cocoate, sorbitan stearate, sorbitan monoisostearate, sorbitan tristearate, sorbitan oleate, sorbitan sesquioleate, methylglucose isostearate, sucrose (poly) palmitostearate, sucrose laurate, sucrose palmitate, sucrose tribehenate, sucrose oleate, sucrose distearate, sucrose polylaurate, sucrose laurate and sucrose hexaerucate, and mixtures thereof, for example Arlatone 2121® sold by the company ICI or Span 65V from the company Uniqema;

esters of fatty acids, especially of $C_8$-$C_{24}$ and preferably of $C_{16}$-$C_{22}$, and of polyol, especially of glycerol or sorbitol, such as glyceryl stearate, sold, for example, under the name Tegin M® by the company Goldschmidt, polyglyceryl diisostearate, polyglyceryl isostearate, polyglyceryl monostearate, diglyceryl tetraisostearate, polyethylene glycol diisostearate, polyglyceryl-10 pentastearate, glyceryl monooleate, glyceryl laurate, such as the product Imwitor 312® by the company Hüls, diethylene glycol (di)laurate, decaglyceryl pentaoleate, decaglyceryl pentadiisostearate, glyceryl caprate/caprylate, polyglyceryl-2 (iso)stearate and (poly)ricinoleate;

oxyalkylenated alcohols, in particular oxyethylenated and/or oxypropylenated alcohols, which may comprise from 1 to 15 oxyethylene and/or oxypropylene units, in particular ethoxylated $C_8$-$C_{24}$ and preferably $C_{12}$-$C_{18}$ fatty alcohols such as stearyl alcohol ethoxylated with 2 oxyethylene units (CTFA name: Steareth-2 such as Brij 72 sold by the company Uniqema, or oxyethylenated oleyl alcohol;

fatty alcohols such as cetylstearyl alcohol, oxyethylenated and/or oxypropylenated silicone compounds, for example containing from 3 to 20 oxyalkylene units and especially oxyethylenated and/or oxypropylenated dimethicones; it should be noted that when a polyoxyalkylenated or polyglycerolated organopolysiloxane elastomer, referred to as being emulsifying, where appropriate conveyed in a non-volatile oil, as described above, is used, it may simultaneously be the surfactant and the organopolysiloxane elastomer for the composition in accordance with the invention;

the mixture of cyclomethicone/dimethicone copolyol sold under the name Q2-3225C® by the company Dow Corning.

b) anionic surfactants such as:

salts of $C_{16}$-$C_{30}$ fatty acids, especially amine salts, such as triethanolamine stearate or 2-amino-2-methylpropane-1,3-diol stearate;

polyoxyethylenated fatty acid salts, especially animated salts or salts of alkali metals, and mixtures thereof;

phosphoric esters and salts thereof, such as DEA oleth-10 phosphate (Crodafos N 10N from the company Croda) or monopotassium monocetyl phosphate (Amphisol K from Givaudan or Arlatone MAP 160K from the company Uniqema);

sulfosuccinates such as Disodium PEG-5 citrate lauryl sulfosuccinate and Disodium ricinoleamido MEA sulfosuccinate;

alkyl ether sulfates such as sodium lauryl ether sulfate; isethionates;

acylglutamates such as Disodium hydrogenated tallow glutamate (Amisoft HS-21 R® sold by the company Ajinomoto), and mixtures thereof.

c) cationic surfactants, among which mention may be made especially of:

alkylimidazolidiniums such as isostearylethylimidonium ethosulfate, ammonium salts such as ($C_{12-30}$ alkyl)tri($C_{1-4}$ alkyl)ammonium halides, for instance N,N,N-trimethyl-1-docosanaminium chloride (or behentrimonium chloride).

d) amphoteric surfactants, for instance N-acylamino acids such as N-alkyl aminoacetates and disodium cocoamphodiacetate, and amine oxides such as stearamine oxide, or alternatively silicone surfactants, for instance dimethicone copolyol phosphates such as the product sold under the name Pecosil PS 100® by the company Phoenix Chemical; and mixtures thereof.

Preferably, the emulsifying system comprises at least one nonionic surfactant of less than 8 at 25° C., chosen from saccharide esters, preferably a sorbitan stearate, and a polyoxyalkylenated or polyglycerolated silicone compound, preferably a PEG-10 dimethicone, and a mixture thereof.

Preferably, the emulsifying system used in the present invention is other than an emulsifying organopolysiloxane elastomer. Preferably, a composition according to the invention combines an emulsifying system other than an emulsifying organopolysiloxane elastomer with a non-emulsifying organopolysiloxane elastomer.

The composition in accordance with the invention may comprise an emulsifying system, in a content ranging from 0.5% to 10% by weight, preferably from 1% to 5% by weight and even more preferably from 1.5% to 3% by weight relative to the total weight of the said composition.

It is understood that the alkali metal, alkaline-earth metal or transition metal salts, such as zinc stearate, zinc myristate or magnesium stearate, are not considered within the meaning of the present invention as forming an emulsifying system. Specifically, such compounds serve first and foremost as fillers, and in particular as agents for compacting the pulverulent phase.

Chelating Agents

According to one particularly advantageous embodiment, the composition may comprise a chelating agent. Such chelating agents are defined and described in particular in the article "*Chelating agents*" Kirk Othmer Encyclopedia of Chemical Technology, Vol. 5 pp. 708-739, published in 2003.

As mentioned in that article, this agent may be chosen from polyphosphates, aminocarboxylic acids, 1,3-diketones, hydroxycarboxylic acids, polyamines, amino alcohols, heterocyclic aromatic bases, aminophenols, Schiff's bases, tetrapyrroles, sulfur compounds, synthetic macrocyclic compounds, polymers and phosphonic acids.

Preferably, this agent is chosen from aminocarboxylic acids, and is preferably EDTA.

These agents are particularly useful for reducing the electrostatic bonding associated with substantial presence of water in the intermediate makeup and/or care composition according to the invention. To do this, the addition of a sequestrant or of a complexing agent, for instance tetrasodium EDTA, makes it possible to complex the free ions, and more specifically the cations of the type $Ca^{2+}$ (mineral fillers) especially present in the nacres and fillers. Consequently, when EDTA complexes these ions, the ionic strength of the water decreases.

Adjuvants

The composition may comprise other ingredients (adjuvants) usually used in cosmetics, such as preserving agents, cosmetic active agents, moisturizers, UV screening agents, thickeners and fragrances.

Needless to say, a person skilled in the art will take care to select the optional adjuvant(s) added to the composition according to the invention such that the advantageous properties intrinsically associated with the composition in accordance with the invention are not, or are not substantially, adversely affected by the envisaged addition.

Assembly

According to another aspect, the invention also relates to a cosmetic assembly comprising:

i) a container delimiting one or more compartment(s), the said container being closed by a closing member; and ii) a makeup and/or care composition in accordance with the invention placed inside the said compartment(s).

The container may be, for example, in the form of a jar or a box.

The closing member may be in the form of a lid or a tear-off cover. In particular, this closing member may comprise a cap mounted so as to be able to move by translation or by pivoting relative to the container housing the said makeup and/or care composition(s).

EXAMPLES

Two solid cosmetic compositions in compact powder form according to the invention were prepared as follows, and then tested from the point of view of impact strength and wear property.

| Phases | Compounds | % content Pearly | Satiny |
|---|---|---|---|
| 1 | Talc (Luzenac Pharma M ® from Luzenac) | qsp | / |
|  | Synthetic fluorphlogopite (Synmica Super C86-3222 ® from Sun) | / | qsp |
|  | Magnesium aluminium silicate (Veegum HV Granules ® from Vanderbilt) | 3 |  |
|  | Zea mays starch (MST ® from LCW Sensient) | 3 |  |
|  | Xanthan gum (Keltrol TF ® from CP Kelco) | 0.1 |  |
|  | Pigments | 0-5 | 30 |
| 2 | Nacres | 55-60 | 30 |
| 3 | Sorbitan stearate (Montane 60 Ecailles ® from SEPPIC) | 2.3 | 2 |
|  | Caprylyl/capric triglyceride (Miglyol 812 N ® from Sasol) | 3.2 | 2.2 |
|  | Dipentaerythrityl tetrahydroxystearate/tetraisostearate (Salacos 168 EV ® from Nisshin Oillio) | 2.6 | 1.8 |
|  | Octyldodecyl stearoyl stearate (Ceraphyl 847 ® from ISP) | 5.1 | 3 |
|  | Caprylyl glycol (Dermosoft Octiol ® from Dr. Straetmans) | 1 |  |
| 4 | Dimethicone and Dimethicone Crosspolymer (KSG 16 ® from Shin-Etsu, containing 24% organopolysiloxane elastomer solids) | 7.8 |  |
|  | Dimethicone and Dimethicone Crosspolymer (DC 9701 Cosmetic Powder ® from Dow Corning, containing 93% organopolysiloxane elastomer solids) | 0.2 |  |

Preparation Process

The procedure below was used to prepare the compositions according to the invention.

1—Preparation of Phase 1:

The compounds of phase 1 and the pigments of phase 1 are weighed out in a stainless-steel crucible and then milled using a shredder, first once for 15 seconds at 1500 rpm and then three times for 1 minute at 3000 rpm.

2—Preparation of Phase 2:

The nacres of phase 2 are weighed out in a second crucible and added to phase 1, and the preparation (phase 1+phase 2) is milled in a shredder (R5 or R5 plus) twice for seconds at 1500 rpm.

3—Incorporation of Phase 3:

The compounds of phase 3 are weighed out in a 250 ml beaker and then heated on a water bath at 75° C. When phase 3 has melted, it is stirred using a deflocculator (Turbotest 33/300 PH—Rayneri, Group VMI) until a vortex forms (about 300 rpm) and then added with stirring via the lid of the shredder once for 1 minute at 1500 rpm to the preparation (phase 1+phase 2).

4—Preparation of Phase 4:

The compounds of phase 4 mixed beforehand with a deflocculator are weighed out in a small stainless steel crucible, added to the rest of the preparation and then milled in a shredder, first once for 1 minute at 1500 rpm and then twice for 2 minutes at 3000 rpm and finally once for 1 minute at 3000 rpm.

5—Finishing of the Preparation:

The powder obtained is then diluted in demineralized water. The amount of water is between 30% and 50% by weight relative to the total weight of the composition so as to obtain a viscosity suitable for a Pilote Back Injection machine sold by the company Nanyo Co. Ltd. This Back Injection machine makes it possible to obtain the "powder-water" mixture, also known as a slurry, via the base of the cup and simultaneously to draw off part of the dilution water by suction. Throughout the injection of the product, the injection mould is placed under vacuum so as to allow the removal of the water, which is drawn off by suction and recovered in the vacuum trap. Placing under vacuum thus promotes the filling and homogenization of the cup. The parts back-injected are then placed in a ventilated oven at 50° C. until their weight no longer changes. The product is then considered as being dry.

Measurement of the Impact Strength

Measurement Principle

The machine for taking such a measurement, known as a Packaging Drop Test machine from the company Co. Pack (Italy), makes it possible to perform drop tests on solid compositions in compact powder form to measure their impact strength. The drop height is 30 cm. Using a ruler, the size of the support that maintains the compact is set (according to the size of the cup) and the compact is then dropped by means of compressed air that actuates the opening of the support.

This machine replaces the manual drop tests performed previously by the formulator using a 30 cm ruler. In this new way, they are repeatable and thus more reliable.

These drop tests are also included in the study of the stability of the compacts prepared.

Results:

An eyeshadow (ES) obtained via a conventional compacting process, during which the pulverulent phase is mixed with a fatty phase and the whole is then compacted, generally withstands a number of drops of between 3 and 8, with a maximum of 45% nacres. By means of the various tests performed on the nacreous shades (containing more than 55% nacres), it was observed that the compact powders according to the invention withstand a number of drops of between 10 and 20. This number is much higher than that of a compact powder with a higher percentage of nacres. The strength of the finished product has thus indeed been improved.

This improvement in the impact strength is explained according to the inventors by the particular structuring of the solid composition according to the present invention by the hydrophilic gelling agents and the emulsifying system, which makes it possible to obtain a compact powder that is stronger than a compact powder obtained via the conventional processes not including such compounds. Furthermore, the water that serves for dilution and for forming is very important, since it is that which creates the cohesion.

Measurement of the Wear Property with Wet Application:

A measuring protocol was performed on 12 people and the results evaluated by 10 judges.

Measurement Principle

1—Makeup removal performed the evening before;

2—A photo without makeup taken (0%);

3—Application of ES with a wet applicator by 10 wipes over the powder and then 10 wipes onto the eyelid, operation repeated twice;

4—A photo taken at T0h of 100%;

5—A photo taken at T7h;

6—The photos of the products, taking the 100% as reference, are evaluated by the naked eye under blind conditions, so as to give each product an estimation of the percentage of wear at 7h between 0 and 100% in intervals of 10%.

Result

The results obtained with the composition according to the invention applied wet show that the wear property of the ES according to the invention is very good. Specifically, after 7h of application, during which the panellists are not subjected to any constraint, 80% to 100% of product remains on the eyelid after this period.

Another test performed under the same conditions moreover shows that a wet application of a conventional ES (*Ombre á Paupiéres Duo Lumiére* from YSL) does not modify its wear property, in contrast with that of an ES according to the invention, the wear property of which is significantly improved.

Finally, another test performed under conditions similar to those outlined above, the only difference being that the applicator remains dry, showed that the wear property on dry application of an ES according to the invention is very good but comparable to that of a conventional ES (*Ombre á Paupiéres Duo Lumiére* from YSL).

It is understood that, in the context of the present invention, the weight percentages given for a compound or a family of compounds are always expressed as weight of solids of the compound in question.

Throughout the application, the term "comprises one" or "includes one" should be understood as meaning "comprising at least one" or "including at least one", unless otherwise specified.

The invention claimed is:

1. A process for making a composition in the form of a compact powder, wherein the composition comprises:
   at least one pulverulent phase;
   at least one organopolysiloxane elastomer;
   at least one emulsifying system;
   at least one hydrophilic gelling agent selected from the group consisting of thickening fillers, polymeric thickeners and associative polymers; and at least one organic non-volatile oil present in a content of greater than or equal to 1% by weight relative to a total weight of the composition, the process comprising:

preparing an injection molded intermediate composition comprising 30-50% by weight with respect to the total weight of the injection molded intermediate composition of water and a non-volatile phase comprising the pulverulent phase, the organopolysiloxane elastomer, the emulsifying system, the hydrophilic gelling agent and the organic non-volatile oil, injecting the injection molded intermediate composition into a mold, removing at least a portion of the water from the injection molded intermediate composition in the mold under vacuum.

2. The process of claim 1, wherein the composition comprises less than 3% by weight of water relative to the total weight of the composition.

3. The process of claim 1, wherein the composition has a solid content of greater than or equal to 95%.

4. The process of claim 1, wherein the composition comprises a pulverulent phase in an amount of greater than or equal to 35% by weight relative to the total weight of the composition.

5. The process of claim 1, wherein the pulverulent phase comprises a filler and a coloring agent, wherein the coloring agent is at least one selected from the group consisting of a nacre, a pigment, reflective particles, and mixtures thereof.

6. The process of claim 1, wherein the pulverulent phase comprises nacres in a content of between 30% and 70% by weight relative to the total weight of the composition.

7. The process of claim 1, wherein the emulsifying system comprises at least one surfactant selected from the group consisting of a nonionic surfactant with a Griffin hydrophilic-lipophilic balance value of less than 8 at 25° C., an anionic surfactant, a cationic surfactant and an amphoteric surfactant.

8. The process of claim 1, wherein the emulsifying system comprises at least one surfactant selected from the group consisting of a saccharide ester, a saccharide ether, a fatty acid ester, an oxyalkylenated alcohol, a fatty alcohol and a silicone compound.

9. The process of claim 1, wherein the organopolysiloxane elastomer is non-emulsifying.

10. The process of claim 1, wherein the organopolysiloxane elastomer is present in a solid content by weight of between 0.5% and 8% relative to the total weight of the composition.

11. The process of claim 1, wherein the non-volatile oil is a hydrocarbon-based non-volatile oil, a silicone non-volatile oil, or a mixture thereof.

12. The process of claim 1, wherein the composition further comprises a chelating agent.

13. The process of claim 1, wherein the composition is an eyeshadow, a foundation powder or a blusher.

14. The process of claim 1, wherein the composition has a pressure resistance of 0.2 kg to 2.5 kg.

15. The process of claim 1, wherein the hydrophilic gelling agent is at least one selected from the group consisting of clays, xanthan gum, 2-acrylamido-2-methylpropane sulfonic acid/acrylamide copolymers and nonionic associative polyurethane polyether-based polymers.

* * * * *